United States Patent
Miyazaki et al.

(10) Patent No.: US 9,433,391 B2
(45) Date of Patent: Sep. 6, 2016

(54) SCINTILLATOR AND RADIATION DETECTION DEVICE

(71) Applicant: KABUSHIKI KAISHA TOSHIBA, Tokyo (JP)

(72) Inventors: Kazunori Miyazaki, Kanagawa (JP); Rei Hasegawa, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 14/847,276

(22) Filed: Sep. 8, 2015

(65) Prior Publication Data
US 2016/0073983 A1 Mar. 17, 2016

(30) Foreign Application Priority Data
Sep. 17, 2014 (JP) .................................. 2014-189323

(51) Int. Cl.
| G01T 1/20 | (2006.01) |
| A61B 6/00 | (2006.01) |
| A61B 6/03 | (2006.01) |
| G01T 1/24 | (2006.01) |
| H04N 5/32 | (2006.01) |

(52) U.S. Cl.
CPC ............. *A61B 6/4241* (2013.01); *A61B 6/032* (2013.01); *A61B 6/482* (2013.01); *G01T 1/2002* (2013.01); *G01T 1/2006* (2013.01); *G01T 1/2018* (2013.01); *G01T 1/248* (2013.01); *H04N 5/32* (2013.01); *A61B 6/5205* (2013.01)

(58) Field of Classification Search
CPC .. A61B 6/4241; G01T 1/2002; G01T 1/2006
See application file for complete search history.

(56) References Cited

U.S. PATENT DOCUMENTS

| 7,403,589 B1 | 7/2008 | Short et al. | |
| 8,319,185 B2 | 11/2012 | Ronda | |
| 2005/0274916 A1* | 12/2005 | Shoji | B32B 3/00 250/580 |
| 2008/0277588 A1* | 11/2008 | Zeitler | G01T 1/202 250/370.11 |
| 2010/0320389 A1* | 12/2010 | Tonami | G01T 1/1644 250/361 C |
| 2011/0056063 A1* | 3/2011 | Tonami | G01T 1/1644 29/428 |
| 2013/0048866 A1* | 2/2013 | Nishino | G01T 1/202 250/366 |
| 2013/0153775 A1 | 6/2013 | Nomura et al. | |
| 2014/0254752 A1* | 9/2014 | Selim | G01N 23/223 378/44 |

FOREIGN PATENT DOCUMENTS

| JP | 11-211836 | 8/1999 |
| JP | 2008-246206 | 10/2008 |
| JP | 2010-515075 | 5/2010 |
| JP | 2010-127900 | 6/2010 |
| JP | 2010-210580 | 9/2010 |
| JP | 2013-029356 | 2/2013 |
| JP | 2013-127371 | 6/2013 |
| JP | 2015-075376 | 4/2015 |

\* cited by examiner

*Primary Examiner* — Mark R Gaworecki
(74) *Attorney, Agent, or Firm* — Finnegan, Henderson, Farabow, Garrett & Dunner LLP

(57) ABSTRACT

According to an embodiment, a scintillator includes a scintillator layer and a radiation absorption layer. Scintillation photons corresponding to incident radiation are generated in the scintillator layer. The radiation absorption layer is laminated to the scintillator layer. The radiation absorption layer faces a detecting surface of a detector that detects the scintillation photons.

2 Claims, 7 Drawing Sheets

BODY AXIS DIRECTION
(M NUMBER OF ROWS)

CHANNEL DIRECTION
(N NUMBER OF COLUMNS)

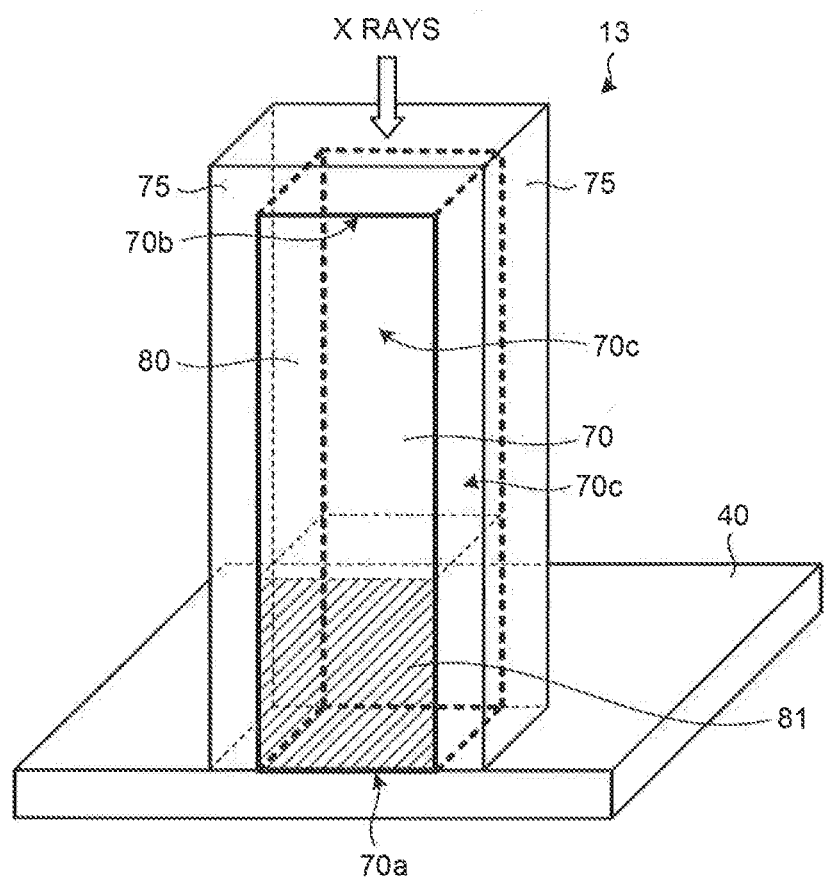

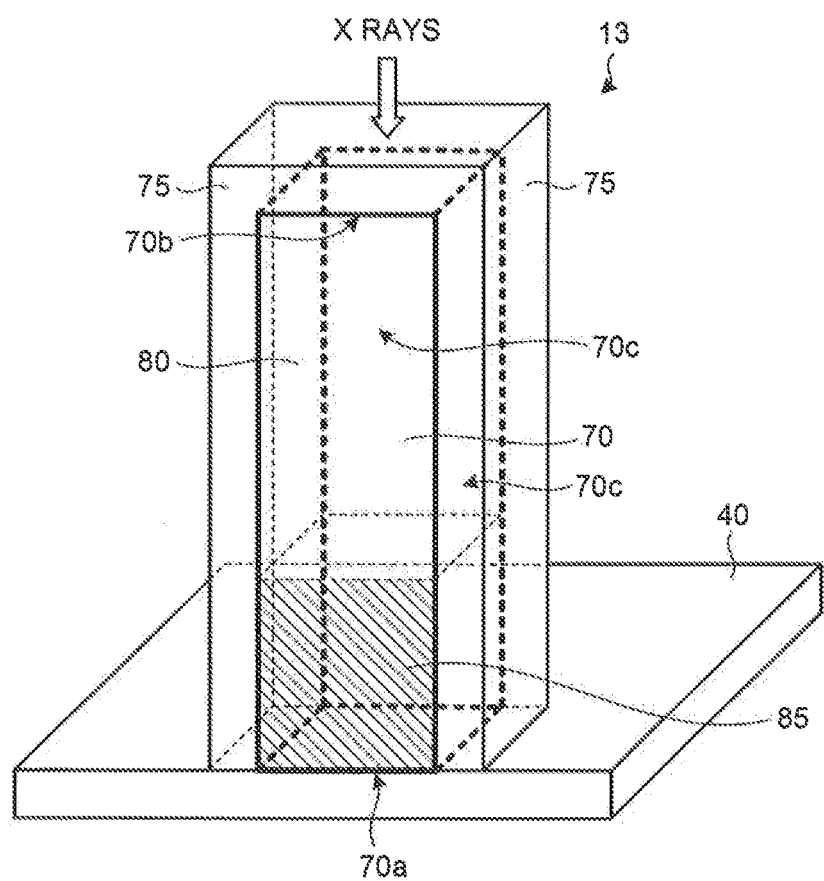

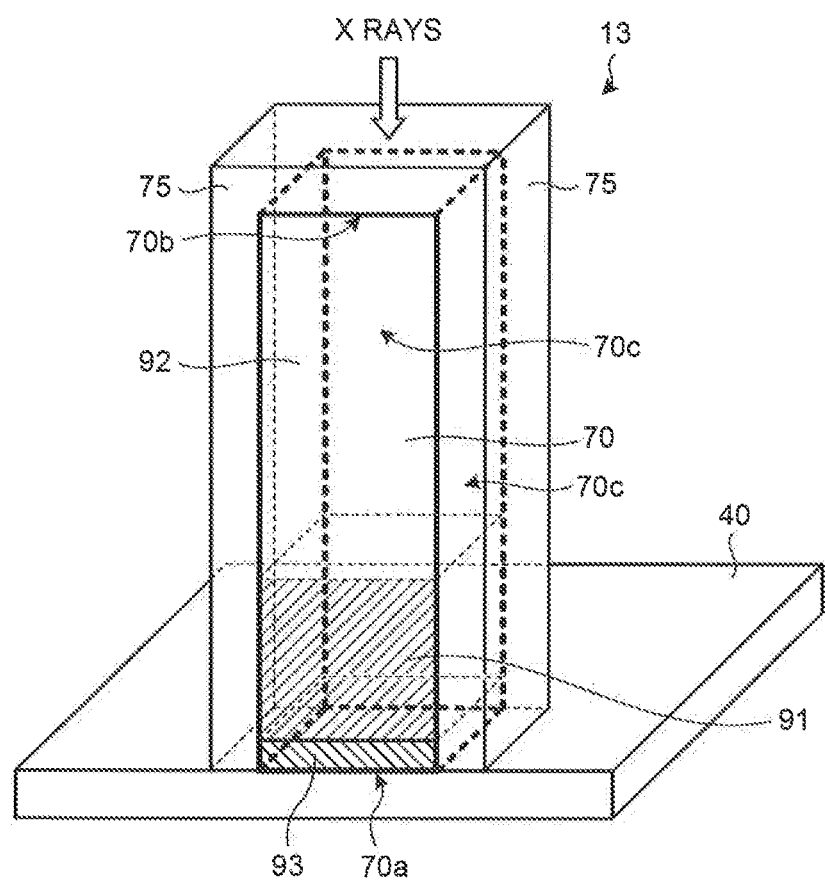

SCINTILLATOR AND RADIATION DETECTION DEVICE

CROSS-REFERENCE TO RELATED APPLICATION

This application is based upon and claims the benefit of priority from Japanese Patent Application No. 2014-189323, filed on Sep. 17, 2014 the entire contents of which are incorporated herein by reference.

FIELD

Embodiments described herein relate generally to a scintillator, a radiation detection device, and a radiation inspection.

BACKGROUND

In the present day, a photon counting CT device (CT stands for Computed Tomography) is known in which a photon counting type detector is used. Unlike a charge integrating detector, the photon counting type detector is configured to detect individual X-ray photons that have passed through a test subject. Thus, in the photon counting CT device, it is possible to reconstruct X-ray CT images having a high signal-to-noise (S/N) ratio.

Moreover, the photon. counting type detector can be used in measuring (discriminating) the energies of X-ray photons. Hence, in the photon counting CT device, projection data, which is collected. by irradiation of X-rays from an X-ray tube with one type of tube voltage, can be divided into a plurality of energy components and image formation can be performed.

As a detector of the photon counting type, an "indirect-conversion-type detector" is known in which the incident X-ray photons are temporarily converted into visible light (a scintillator light) using a scintillator and then the scintillator light is converted, into electrical signals using an optical sensor, An optical sensor detects individual scintillation photons that are obtained by a scintillator by conversion from radiation, and detects the radiation failing on the scintillator and measures the energy of that radiation. Examples of the optical sensor include a sensor in which a plurality of avalanche photo diodes (APDs), which operate in the Geiger mode, is arranged in an array.

In order to measure the energy of radiation, it is important to accurately measure the number of scintillation photons that are generated. The scintillation photons generated in a scintillator are incident, directly on a photon counting sensor. Alternatively, the scintillation photons repeatedly get reflected from a lateral face or the top face of the scintillator and then are incident on the photon counting sensor. It is often the case that the scintillation photons are generated in the vicinity of the radiation incidence plane of the scintillator. In that case, there is a little distance between the position of generation of the scintillation photons and the position of the photon counting sensor. Hence, the scintillation photons fall on the photon counting sensor in a uniform manner (i.e., fall substantially on the entire photon counting sensor with an appropriate spread).

However, in case the scintillation photons are generated in the vicinity of the interface of the scintillator and the photon counting sensor, a majority of the scintillation photons are incident locally on the photon counting sensor. As a result, it becomes difficult to accurately count the scintillation photons.

BRIEF DESCRIPTION OP THE DRAWINGS

FIG. 5 is a perspective view of a scintillator that is installed in the detector of the photon counting CT device according to the first embodiment;

FIG. 6 is a perspective view of a scintillator that is installed in the detector of a photon counting CT device according to a second embodiment;

FIG. 7 is a perspective view of a scintillator that is installed in the detector of a photon counting CT device according to a third embodiment;

Figure 8A:
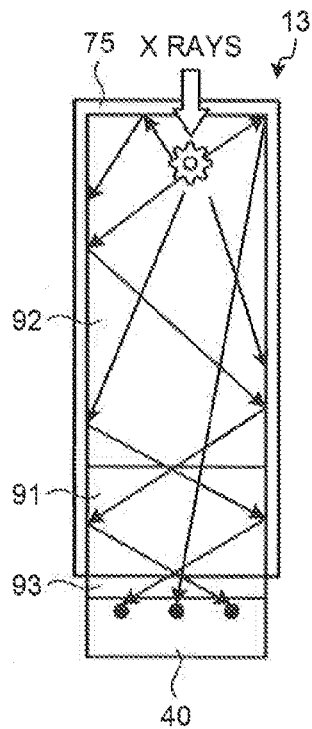
Figure 8B:
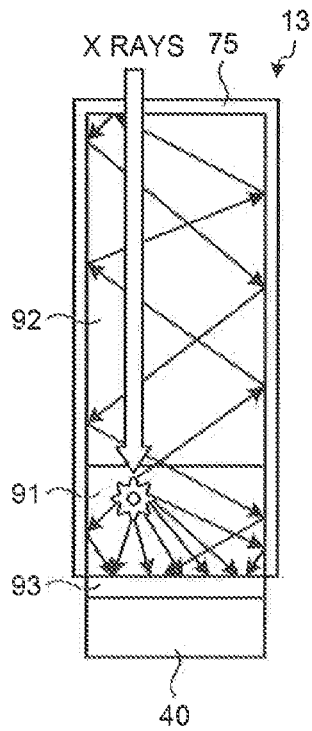

FIG. 8A is a diagram illustrating a condition in the photon counting CT device according to the third embodiment in which scintillation photons generated at a distant position from the interface of the scintillator and the detector fall diffusely on a detecting element; and FIG. 8B is a diagram illustrating a condition in the photon counting CT device according to the third embodiment in which scintillation photons generated in the vicinity of the interface of the scintillator and the detector are prevented from falling on the detecting element.

DETAILED DESCRIPTION

According to an embodiment, a scintillator includes a scintillator layer and a radiation absorption layer. Scintillation photons corresponding to incident radiation are generated in the scintillator layer. The radiation absorption layer is laminated to the scintillator layer. The radiation absorption layer faces a detecting surface of a detector that detects the scintillation photons.

Exemplary embodiments of a photon counting CT device (CT stands for Computed Tomography), in which scintillator, a radiation detection device, and a radiation inspection device are implemented, are described below in detail with reference to the accompanying drawings.

First Embodiment

In a photon counting CT device that is an example of a radiation inspection device, the X-ray photons that have passed through a test subject are counted using a detector of the photon counting type, and X-ray CT image data having a high signal-to-noise (S/N) ratio is reconstructed. Each individual X-ray photon has a different energy. The photon counting CT device measures the energy values of the X-ray photons, and obtains the information about the energy components of the X-rays. Moreover, the photon counting CT device divides projection data, which is collected by driving an X-ray tube with one type of tube voltage, into a plurality of energy components and forma an image.

Figure 1:
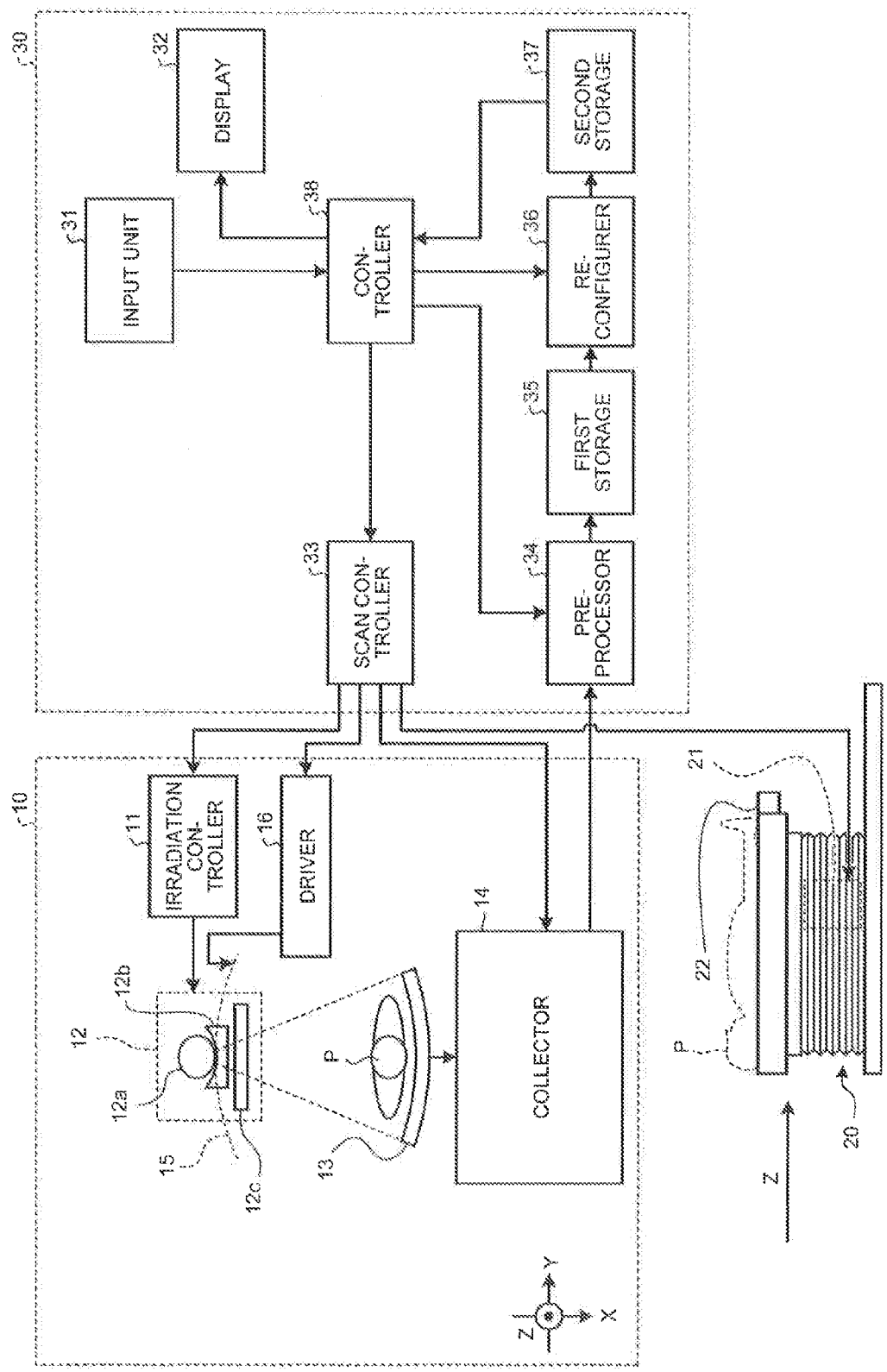
FIG. 1 is a diagram illustrating a configuration of a photon counting CT device according to a first embodiment.

In FIG. 1 is illustrated a configuration of the photon counting CT device according to a first embodiment. As illustrated in. FIG. 1, the photon counting CT device includes a mount device 10, a berth device 20, and a console device 30.

The mount device 10 includes an irradiation controller 11, an X-ray generating device 12, a detector 13, a collector 14, a rotating frame 15, and a driver 16. The mount device 10 irradiates X-rays over a test subject P and counts the X-rays that have passed through the test subject P.

The rotating frame 15 supports the X-ray generating device 12 and the detector 13 in such a way that the X-ray generating device 12 and the detector 13 are positioned opposite to each other across the test subject P. Moreover, the rotating frame 15 is a ring-shaped frame rotated at high speeds in a circular path around the test subject P by the driver 16 (described later).

The X-ray generating device 12 includes an X-ray tube 12a, a wedge 12b, and a collimator 12c. The X-ray generating device 12 is a device that generates X-rays and irradiates the X-rays over the test subject P. The X-ray tube 12a is a vacuum tube for emitting X-rays corresponding to a high voltage supplied from the X-ray generating device 12 (described later). The X-ray tube 12a keeps rotating according to the rotation of the rotating frame 15 and irradiates X-ray beams over the test subject P. Meanwhile, the X-ray tube 12a generates X-ray beams that expand with a fan angle and a cone angle.

The wedge 12b is an X-ray filter used in adjusting the dosage of the X-rays emitted from the X-ray tube 12a. More particularly, through the wedge 12b, the X-rays emitted from the X-ray tube 12a pass and undergo attenuation in such a way that the X-rays irradiated toward. the test subject P have a predetermined distribution.

For example, the wedge 12b is a filter made by processing aluminum to have a predetermined target angle and a predetermined thickness. A wedge is also called a wedge filter or a bow-tie filter. The collimator 12c is a slit that, under the control of the irradiation controller 11 (described later), narrows the range of irradiation of the X-rays for which the wedge 12b has adjusted the X-ray dosage.

The irradiation controller 11 functions as a high-voltage generator that supplies a high voltage to the X-ray tube 12a. Thus, the X-ray tube 12a generates X-rays using the high voltage supplied from the irradiation controller 11, Moreover, the irradiation controller 11 adjusts the tube voltage or the tube current supplied to the X-ray tube 12a and adjusts the X-ray dosage with which the test subject P is irradiated. Furthermore, the irradiation controller 11 adjusts the aperture of the collimator 12c so as to adjust the range of irradiation (the fan angle or the cone angle) of the X-rays.

The driver 16 rotary-drives the rotating frame 15 so that the X-ray generating device 12 and the detector 13 swirl on a circular path around the test subject P. Every time there is incoming radiation of X-ray photons, the detector 13 outputs signals that enable measuring the energy values of those X-ray photons. The X-ray photons referred to herein are, for example, the X-ray photons that are emitted from the X-ray tube 12a and that have passed through the test subject P. The detector 13 includes a plurality of detecting elements that, every time there is incoming radiation of an X-ray photon, outputs a single-pulse electrical signal. The detecting elements are, for example, photoelectric conversion elements. By counting the number of electrical signals (pulses), it becomes possible to count the number of X-ray photons incident on each detecting element. Moreover, by performing predetermined arithmetic processing with respect to those signals, it becomes possible to measure the energy values of the X-ray photons that prompted the output of the signals.

Herein, the detector 13, which is an example of a radiation detection device, is an "indirect-conversion-type detector". Thus, in the detector 13, the incident X-ray photons are temporarily converted into visible light (a scintillator light) using a scintillator and then the scintillator light is converted into electrical signals using detecting elements such as photomultiplier tubes.

Figure 2:
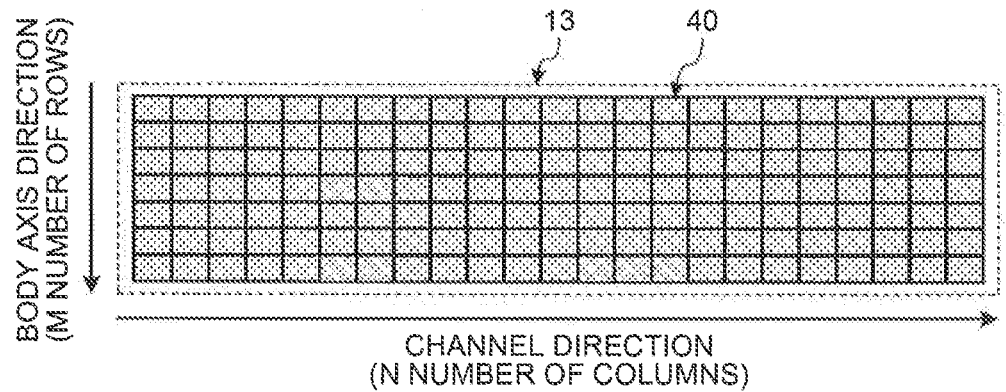
FIG. 2 is a planar view of a detector installed in the photon counting CT device according to the first embodiment.

In FIG. 2 is illustrated an example of the detector 13. Herein, the detector 13 is a plane detector in which detecting elements 40, each of which is made of a photomultiplier tube having a scintillator, are disposed for N number of columns in a channel direction (in the Y-axis direction with reference to FIG. 1) and for M number of rows in a body axis direction (in the z-axis direction with reference to FIG. 1). Corresponding to the incidence of photons, the detecting elements 40 output single-pulse electrical signals. Then, by differentiating the individual pulses output by the detecting elements 40, it becomes possible to count the number of X-ray photons that are incident on the detecting elements 40. Moreover, by performing arithmetic processing based on the intensities of the pulses, it becomes possible to measure the energy values of the X-ray photons that have been counted.

Meanwhile, although not illustrated in FIG. 2, at the subsequent stage of the detector 13, an amplifier is disposed for each group of a plurality of detecting elements. Each amplifier amplifies the electrical signal output from the detecting elements 40 present at the previous stage, and outputs the amplified signals to the collector 14 illustrated in FIG. 1.

The collector 14 collects counting information, which represents the result of a counting operation performed using the output signals of the detector 13. That is, the collector 14 differentiates the individual signals output from the detector 13 and collects the counting information. Herein, the counting information represents the information that is collected from the individual signals output by the detector 13 (the detecting circuits 40) at every instance of incoming radiation of an X-ray photon which was emitted from the X-ray tube 12a and which has passed through the test subject P. More particularly, in the counting information, the enumerated data of the X-ray photons, which are incident on the detector 13 (the detecting elements 40), is held in a corresponding manner to the energy values of the X-ray photons. Meanwhile, the collector 14 sends the collected counting information to the console device 30.

That is, for each predetermined period of time, the collector 14 collects, as the counting information, the incident positions (the detection positions) of the X-ray photons counted by if the pulses output by the detecting elements 40; the enumerated data; and the energy values of those X-ray photons. For example, as an incident position, the collector 14 collects the position of each detecting element 40 that outputs a pulse (an electrical signal) used in the counting. Moreover the collector 14 can also perform predetermined arithmetic processing with respect to the electrical signals.

The berth device 20 illustrated in FIG. 1 is a device on which the test subject P is made to lie down, and includes top panel 22 and a berth driving device 21. The top panel 22 is a panel on which the test subject is made to lie down. The berth driving device 21 moves the top panel 22 in the Z-axis direction so that the test subject P moves inside the rotating frame 15.

The mount device 10 performs, for example, helical scanning in which the rotating frame 15 is rotated while moving the top panel 22 so that the test subject P is scanned in a helical manner. Alternatively, the mount device 10 performs conventional scanning in which, after the top panel 22 is moved, the rotating frame 15 is rotated while keeping the position of the test subject P fixed so that the test subject P is scanned in a circular path. still alternatively, the mount device 10 performs conventional scanning by implementing the step and shoot method in which the position of the top panel 22 is moved at regular intervals and the conventional scanning is performed at a plurality of scan areas.

The console device 30, which is an example of an image generator, includes an input unit 31, a display 32, a scan controller 33, a preprocessor 34, a first storage 35, a reconstructor 36, a second storage 37, and a controller 38. The console device 30 receives operations performed by an operator with respect to the X-ray CT device as well as reconstructs X-ray CT images using the counting information collected by the mount device 10.

The input unit 31 includes a mouse or a keyboard that is used by the operator of the X-ray CT device for the purpose of inputting various instructions and various settings; and transfers the instructions and the settings, which are received from the operator, to the controller 38. For example, from the operator, the input unit 31 receives imaging conditions related to X-ray CT image data, reconstruction conditions at the time of reconstructing the X-ray CT image data and image processing conditions with respect to the X-ray CT image data.

The display 32 is a monitor device referred to by the operator. Under the control of the controller 38, the display 32 displays the X-ray CT image data as well as displays a graphic user interface (GUI) that enables the operator to input various instructions and various settings via the input unit 31.

The scan controller 33 controls the operations of the irradiation controller 11, the driver 16, the collector 14, and the berth driving device 21 under the control of the controller 38; and controls the counting information collecting operation in the mount device 10.

The preprocessor 34 generates projection data by performing correction operations such as logarithmic conversion, offset correction, sensitivity correction, and beam hardening correction with respect to the courting information sent from the collector 14.

The first storage 35 is used to store the projection data generated by the preprocessor 34. That is, the first storage 35 is used to store the projection data (i.e., the corrected counting information) that is used in reconfiguring the X-ray CT image data.

The reconstructor 36 reconstructs the X-ray CT image data using the projection data stored in the first storage 35. Herein, the reconstruction car be performed by implementing various methods such as the back projection method. Examples of the back projection method. include the filtered back projection (FBP). Moreover, the reconstructor 36 performs variety of image processing with respect to the X-ray CT image data, and generates image data. Then, the reconstructor 36 stores the reconstructed X-ray CT image data and the image data, which is generated by performing a variety of image processing, in the second storage 37.

The projection data that is generated from the counting information, which is obtained during the photon counting CT, contains energy information of the X-rays that have passed through the test subject P. Hence, for example, the reconstructor 36 can reconfigure the X-ray CT image data of particular energy components. Moreover, for example, the reconstructor 36 can reconfigure the X-ray CT image data of each of a plurality of energy components.

Furthermore, for example, according to each energy component, the reconstructor 36 can assign a color tone to each pixel of the X-ray CT image data of that energy component; and can generate a plurality of sets of X-ray CT image data that is color coded according to the energy components. Moreover, the reconstructor 36 can generate image data by superposing these sets of X-ray CT image data.

The controller 38 controls the operations of the mount device 10, the berth device 20, and the console device 30; and performs the overall control of the X-ray CT device. More particularly, the controller 3a controls the scan controller 33 so as to control the CT scanning performed in the mount device 10. Moreover, the controller 38 controls the preprocessor 34 and the reconstructor 36 so as to control the image reconfiguration operation and the image generation operation performed in the console device 30. Furthermore, the controller 38 performs control to display a variety of image data, which is stored in the second storage 37, on the display 32.

Figure 3:
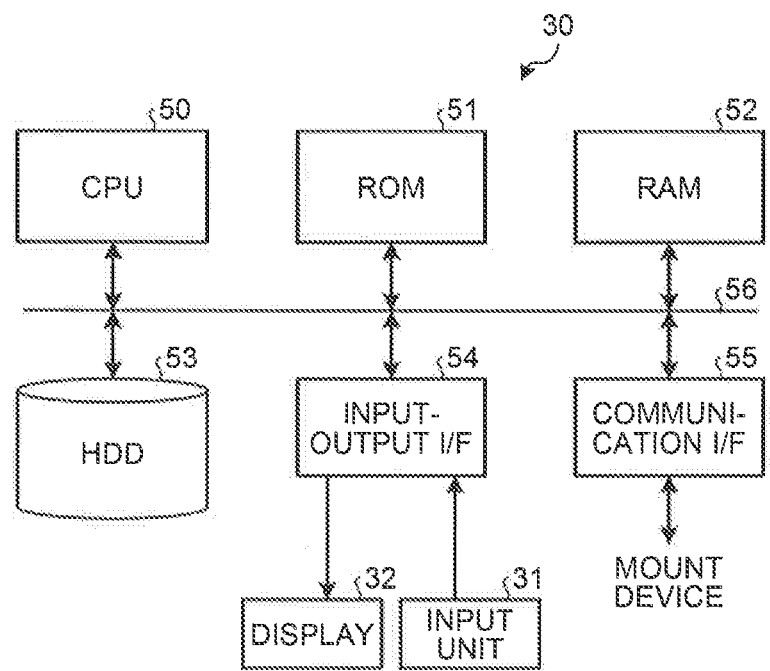
FIG. 3 is a hardware configuration diagram of a console device in the photon counting CT device according to the first embodiment.

The console device 30 can have the hardware configuration illustrated in FIG. 3 as an example. In the example illustrated in FIG. 3, the console device 30 includes a CPU 50, a ROM 51, a RAM 52, an HDD 53, an input-output I/F 54, a communication I/F 55, the input unit 31, and the display 32. Herein, CPU stands for Central Processing Unit; ROM stands for Read Only Memory; RAM stands for Random Access Memory; HDD stands for Hard Disk Drive; and I/F stands for Interface.

The CPU 50, the ROM 51, the RAM 52, the HDD 53, the input-output I/F 54, and the communication I/F 55 are connected to each other via a bus line 56. The input unit 31 and the display 32 are connected to the CPU 50 via the input-output I/F 54. The communication I/F 55 is connected to the mount device 10. The CPU 50 is equivalent to the scan controller 33, the preprocessor 34, the reconstructor 36, or the controller 38. The ROM 51, the RAM 52, and the HDD 53 are equivalent to the first storage 35 or the second storage 37.

Figure 4A:
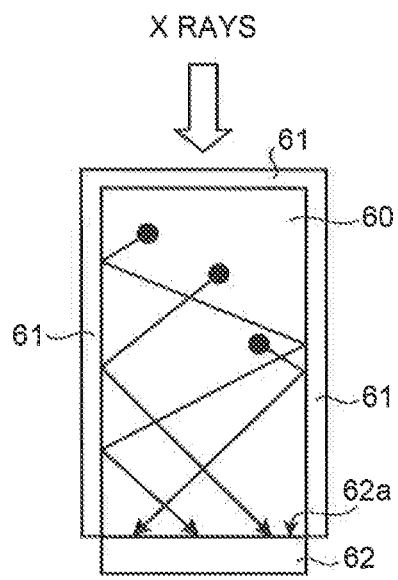
FIG. 4A is a diagram illustrating a condition in which scintillation photons generated at a distant position from the interface of a scintillator and the detector fall diffusely on a detecting element.
Figure 4B:
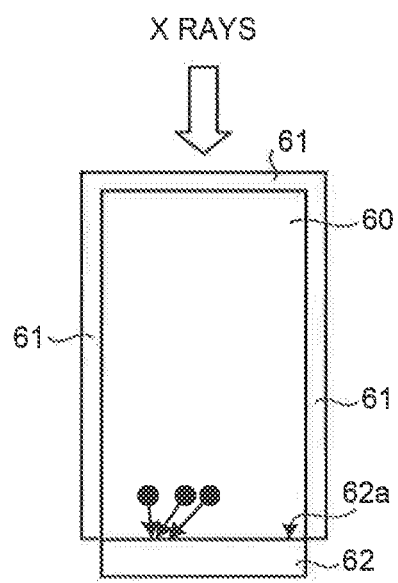
FIG. 4B is a diagram illustrating a condition in which a majority of scintillation photons generated in the vicinity of the interface of the scintillator and the detector fall locally on the detecting element.

In FIGS. 4A and 4B are illustrated exemplary partial cross-sectional views of a commonly-used indirect-conversion-type detector that is cut along the incident direction of the X-rays. FIG. 4A is a diagram illustrating a condition in which scintillation photons generated at a distant position from the interface of a scintillator and the detector fall diffusely on a detecting element. FIG. 4B is a diagram illustrating a condition in which a majority of scintillation photons generated in the vicinity of the interface of the scintillator and the detector fall locally on the detecting element.

In the indirect-conversion-type detector illustrated in FIGS. 4A and 4B, a scintillator 60 is attached to each detecting element 62, and each scintillator 60 is entirely covered by a reflection film 61. Since the X-rays irradiated during projection or imaging have large amount of X-ray energy, the X-rays pass through the reflection film 61 and fall on the scintillator 60, which results in the occurrence of scintillation. The X-rays that fall on the scintillator 60 are converted into, for example, visible light (scintillation photons) that falls on the corresponding detecting element 62.

More particularly, as illustrated in FIG. 4A, when scintillation occurs in the vicinity of the X-ray incidence plane, the scintillation photons fall on the detecting element 62 either after being reflected inside the scintillator 60 due to the corresponding reflection film 61 or directly. Hence, when scintillation occurs in the vicinity of the X-ray incidence plane, the scintillation photons fall on a detecting surface 62a of the detecting element 62 in a substantially uniform manner. That is, the scintillation photons fall on the entire detecting surface 62a of the detector in a substantially uniform manner.

In contrast, as illustrated in FIG. 4B, when scintillation occurs in the vicinity of the joining surface of the scintillator 60 and the detecting element 62 (i.e., in the vicinity of the emission surface of scintillation photons), a majority of scintillation photons fall substantially directly on the detecting element 62. Hence, when scintillation occurs in the vicinity of the interface of the scintillator 60 and the detecting element 62, the scintillation photons fall locally on the detecting surface 62a of the detecting element 62.

The detecting element 62 is configured with a plurality of avalanche photo diodes (APDs), each of which counts the incident scintillation photons (i.e., performs photon counting). However, after the photon counting is performed once, the APDs require a little period of time (preparation period) for again performing photon counting. Hence, if the scintillation photons are incident only locally, a majority of scintillation photons fall on the detector during the preparation period in which counting is difficult to perform. As a result, it becomes difficult to accurately count the scintillation photons.

Regarding the scintillation, the frequency of occurrence is high in the vicinity of the X-ray incidence plane of the scintillator 60, but decreases with distance from the X-ray incidence plane. However, it is a difficult task to control the location of occurrence of scintillation in the scintillator 60.

With the aim of holding down the occurrence of scintillation in the vicinity of the interface of the detector and the scintillator 60, it is possible to think of increasing the thickness of the scintillator 60. In that case, the distance between the incidence plane and the interface increases, and the occurrence of scintillation in the vicinity of the interface is believed to he reducible. However, in this case, due to an increase in the distance between the incidence plane and the interface, there occurs en increase in the number of times for which the scintillation photons get reflected in the scintlliator 60. For that reason, it becomes highly likely that the scintillation photons are absorbed in the scintillator 60 before and instead of falling on the detector.

FIG. 5 is a perspective view of a scintillator 70 that is installed in the detector of the photon counting CT device according to the first embodiment. In the detector 13 illustrated in FIG. 5, as an example, a plurality of prismatic scintillators 70 is disposed. For example, the detecting elements 40 are arranged in a matrix-like manner; and the scintillators 70 are arranged in a matrix-like manner and opposite to the detecting elements 40. Each scintillator 70 has an end face (an incidence plane, a first face) 70b on the side of incidence of the X-rays and has an end face (a second face) 70a positioned opposite to the corresponding detecting element 40. The end faces 70a and 70b lie opposite to each other. In each scintillator 70, of the two end faces representing small areas, the end face 70a is connected to the corresponding detecting element 40.

Meanwnile, in this example, although the scintillators 70 are prismatic in shape, it is also possible to have the scintillators 70 in another shape such as the circular cylindrical shape or the trapezoidal shape. In any case, it is desirable to match the shape and the size of the emission surface of scintillation photons with the shape and size of each detecting element 40.

Moreover the entire scintillator 70, except for the end face 70a that is connected to the detecting element 40 (i.e., except for the emission surface of scintillation photons), is covered by a reflection film 75. That is, in the scintillator 70, the X-ray incidence plane 70b is covered by the reflection film 75. Moreover, in the scintillator 70, all four faces of a periphery 70c are covered by the reflection film 75. FIG. 5, it is illustrated that, in the scintillator 70 having the four-faced periphery 70c, the two mutually opposite faces are covered by the reflection film 75. However, in reality, all four faces of the periphery 70c era covered the reflection film 75.

The reflection film 75 reflects the scintillation photons that are generated due scintillation. In this example, the scintillator 70 converts the incident X rays into visible light. Hence, a reflection film capable of reflecting visible light is used as the reflection film 75. As long as the reflection film 75 is capable of reflecting scintillation photons, it can be made of any type of material. For example, a coating material capable of reflecting scintillation photons can be applied to the scintillator 70. In any case, it is possible to achieve the effect described later.

The scintillator 70 is formed by laminating a scintillator layer 80, which generates scintillation photons corresponding to the incident X rays, and an X-ray absorption layer 81, which absorbs the incident X rays and allows the scintillation photons to pass through. The X-ray absorption layer 81 is an example of a radiation absorption layer. The incident X rays pass through the scintillator 70 at a particular rate depending on the X-ray energy and the thickness of the scintillator 70, and may cause interaction with the detecting element 40 thereby damaging the detecting element 40. In order to reduce that possibility, it is desirable that the incident X rays get absorbed in the X-ray absorption layer 81. As illustrated by hatched lines in FIG. 5, the X-ray absorption layer 81 is formed in the vicinity of the end face 70a that is connected to the detecting element 40. That is, in the example illustrated in FIG. 5, in the scintillator 70, one-third portion starting from the end face 70a serves as the X-ray absorption layer 81. Meanwhile, it is desirable to adjust the thickness of the X-ray absorption layer according to the energy of the incident X rays, the absorption coefficient of the scintillator with respect to the energy of the incident X-rays, and the thickness of the scintillator that is used.

In the scintillator 70, the X-ray absorption layer 81 has a high absorption coefficient with respect to the X rays in the detected energy area and has a high permeability with respect to the light that is generated by the scintillator by absorbing the X rays. For that reason, in the photon counting CT device according to the first embodiment, of the entire scintillator 70, the scintillation photons are generated only in between the end face 70b, on which the X rays are incident, and the X-ray absorption layer 81. Moreover, in the X-ray absorption layer 81 formed in the vicinity of the detecting element 40, scintillation photons are not generated. Thus, the scintillation photons that are generated in the portion other than the X-ray absorption layer 81 pass through the X-ray absorption layer 81 and fall on the detecting element 40. As a result, it becomes possible to prevent an adverse situation in which the scintillation photons that are generated in the vicinity of the detecting element 40 fall locally on the detecting element 40.

As is clear from the explanation given above, in the photon counting CT device according to the first embodiment, of the entire scintillator 70, the portion in the vicinity of the detecting element 40 serves as the X-ray absorption layer Si that absorbs the X rays and allows the scintillation light to pass through. As a result, it becomes possible to prevent an adverse situation in which the scintillation photons that are generated in the vicinity of the detecting element 40 fall locally on the detecting element 40. Moreover, in the scintillator 70, the scintillation photons that are generated at some distance from the detecting element 40 fall on the detecting element 40. Hence, photon counting can be performed while receiving the scintillation, photons that fail on the detecting element 40 in a uniform manner.

Regarding the APDs constituting a detecting element, after the photon counting is performed once, the APDs require a little period of time (preparation period) for again performing photon counting. Hence, if the scintillation photons fall only locally, a majority of scintillation. photons fall on the detector during the preparation period in which counting is difficult to perform. As a result, it becomes difficult to accurately count the scintillation photons.

In contrast, in the photon counting CT device according to the first embodiment, photon counting can be performed while receiving the scintillation photons in a uniform manner over the entire light receiving surface of the detector 13. That makes it possible to accurately count the scintillation photons. Moreover, since it becomes possible to prevent an adverse situation of having to count the scintillation photons falling locally, sue measurement noise can also be prevented from being generated.

Second Embodiment

Given below is the explanation of a photon counting CT device according to a second embodiment. In the explanation of the second embodiment, the explanation is given only about the differences with the first embodiment, and the redundant explanation is not given.

As illustrated in FIG. 6, in the photon counting CT device according to the second embodiment, of the entire scintillator 70, the portion in the vicinity of the detecting element 40 has substantially same composition as the scintillator layer 80 and includes an X-ray absorption layer 85 in which doped components are not included as the luminescence centers. Whether or not doped components are included as the luminescence centers can be measured by performing, for example, non-destructive elemental, analysis of a scintillator using fluorescent X-rays. In the second embodiment, if the measured value is smaller than a predetermined detection lower limit, it is assumed that "doped components are not included as the luminescence center".

In the photon counting CT device according to the second embodiment, the incident X rays are absorbed by the X-ray absorption layer 85, and doped components are not included as the luminescence center in the X-ray absorption layer 85. For that reason, it becomes possible to further prevent an adverse situation in which scintillation photons are generated in the vicinity of the detecting element 40. Besides, it is also possible to achieve the same effect as the effect achieved in the first embodiment.

Third Embodiment

Given below is the explanation of a photon counting CT device according to a third embodiment. In the explanation of the third embodiment, the explanation is given only about the differences with the first and second embodiments, and the redundant explanation is not given.

FIG. 7 is a perspective view of the scintillator 70 that is installed in the detector 13 of the photon counting CT device according to the third embodiment. In the photon counting CT device according to the third embodiment, of the entire scintillator 70, the portion in the vicinity of the detecting element 40 serves as a first scintillator layer 91; while the portion in between the end face 70b, on which the X rays are incident, and the first scintillator layer 91 serves as a second scintillator layer 92. Corresponding to the incident X rays, the first scintillator layer 91 and the second scintillator layer 92 generate scintillation photons having different wavelengths. That is, the first scintillator layer 91 generates first scintillation photons having a wavelength $\lambda 1$ corresponding to the incident X rays. The second scintillator layer 92 generates second scintillation photons of a wavelength $\lambda 2$, which is different than the wavelength $\lambda 1$, corresponding to the incident X rays.

Moreover, in the photon counting CT device according to the third embodiment, in between the first scintillator layer 91 and the detecting element 40, a filter 93 is disposed that either absorbs or reflects only the first scintillation photons, which are generated by the first scintillator layer 91 and which have the wavelength $\lambda 1$, and allows only the second scintillation photons, which are generated by the second scintillator layer 92 and which have the wavelength $\lambda 2$, to pass through.

Thus, in the photon counting CT device according to the third embodiment, as illustrated in FIG. 8A, the second scintillation photons, which are generated by the second scintillator layer 92 and which have the wavelength $\lambda 2$, pass through the filter 93 and fall on the detecting element 40. The second scintillator layer 92 and the detecting element 40 are separated apart by a distance equivalent to the addition of at least the thickness of the first scintillator layer 91 and the thickness of the filter 93. For that reason, the second scintillation photons, which are generated by the second scintillator layer 92 and which have the wavelength $\mu 2$, fall on the detecting element 40 in a substantially uniform manner.

In contrast, the first scintillation photons, which are generated by the first scintillator layer 91 positioned in the vicinity of the detecting element 40 and which have the wavelength $\lambda 1$, get absorbed by the filter 93 as illustrated in FIG. 8B and thus do no fall on the detecting element 40.

That is, in the photon counting CT device according to the third embodiment, corresponding to the X rays falling on the scintillator 70, the first scintillation photons having the wavelength $\lambda 1$ are generated in the vicinity of the detecting element 40. However, the first scintillation photons get absorbed in the filter 93 and thus do not fall on the detecting element 40. The first scintillator layer 91 that is formed in the vicinity of the detecting element 40 serves as a spacing member for maintaining a predetermined distance between the detecting element 40 and the second scintillator layer 92. Because of this predetermined distance, the second scintillation photons, which are generated by the second scintillator layer 92 and which have the wavelength $\lambda 2$, are prevented from falling locally on the detecting element 40.

In this way, in the photon counting CT device according to the third embodiment, the scintillator 70 is formed by laminating the first scintillator layer 91 and the second scintillator layer 92 that generate scintillation photons having different wavelengths. The first scintillator layer 91 is positioned on the side of the detecting element 40, and the filter 93 is disposed in between the first scintillator layer 91 and the detecting element 40 for absorbing the scintillation photons generated by the first scintillator layer 91. As a result, the scintillation photons generated in the vicinity of the detecting element 40 get absorbed. For that reason, it becomes possible to prevent an adverse situation in which scintillation photons fall locally on the detecting element 40. Besides, it is also possible to achieve the same effect as the effect achieved in the first and second embodiments.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the torts or the embodiments described herein may be made without departing from the spirit of the inventions. The accompanying claims and their equivalents are intended to cover such forms or modifications as would fall within the scope and spirit of the inventions.

What is claimed is:

1. A scintillator comprising:
   a first scintillator layer in which first scintillation photons having a first wavelength with respect to incident radiation are generated;
   a second scintillator layer in which second scintillation photons having a second wavelength different from the first wavelength with respect to the incident radiation are generated, the second scintillator layer being laminated to the first scintillator layer; and
   a filter configured to absorb or reflect the first scintillation photons and pass the second scintillation photons through so that the second scintillation photons enter a detecting surface of a detector that detects scintillation photons, the filter being disposed between a scintillation-photon emission surface of the first scintillator layer and the detecting surface of the detector.

2. A radiation detection device comprising:
   the scintillator according to claim 1; and
   the detector configured to receive the scintillation photons from the scintillator.

* * * * *